(12) United States Patent
Nakamura et al.

(10) Patent No.: US 7,632,290 B2
(45) Date of Patent: Dec. 15, 2009

(54) BLOOD VESSEL ANASTOMOSING AUXILIARY TOOL

(75) Inventors: Takasumi Nakamura, Kochi (JP); Manabu Okabe, Kochi (JP); Shigeki Kawarabata, Hiroshima (JP)

(73) Assignee: JMS Co. Ltd., Hiroshima-shi (JP)

( * ) Notice: Subject to any disclaimer, the term of this patent is extended or adjusted under 35 U.S.C. 154(b) by 443 days.

(21) Appl. No.: 10/470,432

(22) PCT Filed: Oct. 23, 2001

(86) PCT No.: PCT/JP01/09283

§ 371 (c)(1),
(2), (4) Date: Aug. 14, 2003

(87) PCT Pub. No.: WO02/058566

PCT Pub. Date: Aug. 1, 2002

(65) Prior Publication Data

US 2004/0073239 A1    Apr. 15, 2004

(30) Foreign Application Priority Data

Jan. 26, 2001 (JP) .............................. 2001-018920
Apr. 25, 2001 (JP) .............................. 2001-127018

(51) Int. Cl.
*A61M 29/00* (2006.01)
(52) U.S. Cl. .................................... 606/191
(58) Field of Classification Search ......... 606/153–156, 606/191; 604/8
See application file for complete search history.

(56) References Cited

U.S. PATENT DOCUMENTS 3,380,609 A    4/1968    Potts 4,168,708 A    9/1979    Lepley, Jr. et al.

(Continued)

FOREIGN PATENT DOCUMENTS

EP    0237021    9/1987

(Continued)

OTHER PUBLICATIONS

European Search Report dated Mar. 25, 2008, issued in corresponding European patent application No. 01978858.

*Primary Examiner*—(Jackie) Tan-Uyen T. Ho
*Assistant Examiner*—Gregory Anderson
(74) *Attorney, Agent, or Firm*—Westerman, Hattori, Daniels & Adrian, LLP

(57) ABSTRACT

A blood vessel anastomosing auxiliary tool consisting of a flexible hollow conduit having opening ends at the opposite ends thereof, and comprising, on the outer surface of the conduit, at least two bulky portions, a retrieving means for retrieving the conduit from within a blood vessel, and desirably a guide wire for guiding the conduit when it is inserted into a blood vessel, characterized in that the conduit has flexibility and self-restoring property, and the bulky portions are disposed on the conduit eccentrically, the use of the blood vessel anastomosing auxiliary tool permitting a quick and positive anastomosis between a bypassed blood vessel and a bypassing blood vessel while a blood flow remaining in a portion between the central and peripheral sides of the bypassed blood vessel is secured during a blood vessel bypassing operation, and further ensuring an unobstructed blood vessel anastomosing to allow an easier practicing operation (anastomosing) than those by conventional tools.

5 Claims, 7 Drawing Sheets

U.S. PATENT DOCUMENTS

| | | | |
|---|---|---|---|
| 4,230,119 A | | 10/1980 | Blum |
| 4,295,464 A | | 10/1981 | Shihata |
| 4,739,768 A | | 4/1988 | Engelson |
| 4,958,634 A | * | 9/1990 | Jang .......................... 606/194 |
| 5,163,905 A | * | 11/1992 | Don Michael ......... 604/101.03 |
| 5,380,284 A | * | 1/1995 | Don Michael ......... 604/101.03 |
| 5,460,610 A | * | 10/1995 | Don Michael ......... 604/101.03 |
| 5,669,880 A | * | 9/1997 | Solar ........................ 623/1.11 |
| 5,807,331 A | * | 9/1998 | den Heijer et al. ..... 604/101.05 |
| 5,868,764 A | | 2/1999 | Rosengart |
| 6,110,187 A | | 8/2000 | Donlon |
| 6,264,633 B1 | | 7/2001 | Knorig |

FOREIGN PATENT DOCUMENTS

| | | |
|---|---|---|
| EP | 0 839 550 A1 | 5/1998 |
| EP | 0 894 507 A2 | 2/1999 |
| EP | 1 022 033 A1 | 7/2000 |
| JP | 52-128681 A | 10/1977 |
| JP | 62-266044 A | 11/1987 |
| JP | 64-072737 A | 3/1989 |
| JP | 02-052641 A | 2/1990 |
| JP | 03-14470 B2 | 2/1991 |
| JP | 04-044555 B2 | 2/1992 |
| JP | 04-261668 A | 9/1992 |
| JP | 05-043390 A | 2/1993 |
| JP | 05-043390 B2 | 2/1993 |
| JP | 10-005231 A | 1/1998 |
| JP | 10-118079 A | 5/1998 |
| JP | 11-000335 A | 1/1999 |
| JP | 2000-005185 A | 1/2000 |
| JP | 2000-5185 A | 1/2000 |
| WO | WO 99/15088 A1 | 4/1999 |

* cited by examiner

BLOOD VESSEL ANASTOMOSING AUXILIARY TOOL

TECHNICAL FIELD

The present invention relates to a blood vessel anastomosing auxiliary tool, especially to a blood vessel anastomosing auxiliary tool to be used for coronary artery bypass operation or blood vessel bypass operation practiced to treat coronary artery diseases.

BACKGROUND ART

It happens that arteriosclerosis or the like cause stenosis in the blood vessel and that blood flow to the peripheral side can be hardly obtain or can not be obtained. In such cases, a bypass operation is practiced, to bypass the stenosis site of the patient's own artery, vein or an artificial blood vessel, and to anastomose the central side and the peripheral side of the vessel.

While practicing this blood vessel anastomosing, in order to obtain a good vision of the anastomotic site, in general, a method of pressing temporarily both ends of the vessel to be anastomosed and to decrease or stop the bleeding from the anostomotic site, was taken conventionally. On the other hand, in case the stenosis site is not completely closed, as blocking blood flow during blood vessel anastomosing may cause adverse effects to the peripheral side, therefore, a method wherein blood flow is secured even during the anastomosing operation is anticipated.

The present inventors have disclosed previously a blood vessel anastomosing auxiliary tool having circular projections (corresponding to the bulky portions of the present invention) on a hollow conduit, as described in Japanese Laid-Open Patent Application No. 11-335. Said auxiliary tool consists of a hollow conduit comprising circular projections (bulky portion) at the ends, and a filamentary retrieving means at the central part, having elasticity to self-restore the hollow conduit bent after it is inserted into a blood vessel.

The use of the above described anastomosing auxiliary tool, have permitted to practice blood vessel anastomosing without completely blocking the blood flow. However, said blood vessel anastomosing auxiliary tool is formed (disposed) so that the shaft center of the conduit (shaft center of the non-bulky portion) and the shaft center of circular cross section formed at the outer edge of the circular projection (corresponding to the bulky portion of the present invention) in the shaft direction of said conduit, are to be substantially the same. Therefore, when the bulky portion of said auxiliary tool is inserted into a blood vessel, as it is shown in FIG. 10, the space formed between the bulky portion and the inner wall of the artery blood vessel to which the tool is inserted, was small, and this was sometime an obstacle when anastomosing blood vessel. That is, when anastomosing blood vessel to another one, when the space was small as shown in FIG. 10, there was a disadvantage that the suture needle would touch the anastomosing auxiliary tool, which caused difficulty for anastomosing.

Furthermore, as for the anastomosing auxiliary tool described in Japanese Laid-Open Patent Application No. 11-335, there was a problem that it was difficult to insert the hollow conduit into a blood vessel. That is, at the time of the operation, it was not easy to insert the above hollow conduit directly into a blood vessel from the opening (incision) of the blood vessel. Therefore, it was necessary to ensure the opening (of the blood vessel) to make the insertion easy.

Moreover, there were several points to improve as for the towing means of the hollow conduit of the anastomosing auxiliary tool of this invention. That is, when retrieving the anastomosing auxiliary tool from the blood vessel after the anastomosis, it is necessary to hold the filamentary towing means and to pull it. However, as it is made from a fine string, it was sometimes difficult to hold it tightly or it happened to drop off the end of the string. Therefore, in order to hold the string or to confirm the end of the string or the like (or to fill out the necessary information), a tool wherein a small plate (tab) is attached on the other end of the string attached to the hollow conduit has also been devised. In this manner, by attaching a tab to the end of the string, it became easier to retrieve the hollow conduit from within the blood vessel. However, as the conventional tab was not designed to be held tightly, it was difficult to hold it tight, and it slipped when moving or pulling the tab with forceps, and it took time to retrieve the hollow conduit (the anastomosing auxiliary tool) from within the blood vessel.

The object of the present invention is to provide a blood vessel anastomosing auxiliary tool that has improved each of the above mentioned problems.

DISCLOSURE OF THE INVENTION

The present invention relates to the amelioration of the blood vessel anastomosing auxiliary tool described in above mentioned Japanese Laid-Open Patent Application No. 11-335, and have resolved each of the above mentioned problems of the blood vessel anastomosing auxiliary tool by the following means.

First, the present invention relates to a blood vessel anastomosing auxiliary tool consisting of at least: a hollow conduit having openings at both ends, having flexibility and self-restoring property for inserting into a blood vessel; a blood leaking preventing means on the outer surface of said hollow conduit, preventing blood leaking from the space formed between the external wall of said conduit and the inner wall of the blood vessel, when the hollow conduit is inserted into a blood vessel; and a retrieving means for retrieving said conduit from within a blood vessel (constituent features of the present invention); and furthermore characterized by: said blood leaking preventing means is 2 or more circular bulky portions disposed on the outer surface of the conduit; and at least 1 of said circular bulky portion is disposed eccentrically against conduit shaft.

Secondly, in addition to the above described constituent features of the blood vessel anastomosing auxiliary tool of the present invention, the present invention relates to a blood vessel anastomosing auxiliary tool, having a flexible guide wire for guiding said hollow conduit when it is inserted into a blood vessel, said guide wire having a higher elasticity than the blood vessel to be inserted, a width being adjustable to be inserted into the lumen of the hollow conduit, and a length being more than 1.2 times longer than the length of the hollow conduit (shaft direction).

Third, the present invention relates to the blood vessel anastomosing auxiliary tool according to the above described constituent features of the blood vessel anastomosing auxiliary tool of the present invention, wherein one end of said retrieving means is attached to said hollow conduit, and to the other end is attached a tab, wherein a holding auxiliary means and an tissue-binding auxiliary means are disposed.

First, the first aspect of the present invention will be explained in detail.

The characteristics of the blood vessel anastomosing auxiliary tool of the present invention is that the tool consists of at least: a hollow conduit having openings at both ends, having flexibility and self-restoring property for inserting into a blood vessel; a blood leaking preventing means on the outer surface of said hollow conduit, preventing blood leaking from the space formed between the external wall of said conduit and the inner wall of the blood vessel, when the hollow conduit is inserted into a blood vessel; and a retrieving means for retrieving said conduit from within a blood vessel; wherein said blood leaking preventing means is 2 or more circular bulky portions disposed on the outer surface of the conduit; and at least 1 of said circular bulky portion is disposed eccentrically against conduit shaft.

With the above described feature, "at least 1 of said bulky portion is disposed eccentrically against conduit shaft", it becomes possible to practice the anastomosing operation easier and with accuracy. In other words, by using a blood vessel anastomosing auxiliary tool wherein the shaft center of the bulky portion is disposed to be different from the shaft center of the conduit (FIGS. 1-9), compared to a blood vessel anastomosing auxiliary tool wherein the bulky portion are not disposed eccentrically on the conduit (FIGS. 10, 11), the space 5 formed between the inner wall of the blood vessel 11 and the anastomosing auxiliary tool 1 (non-bulky portion 3 of the conduit between the 2 bulky portions) becomes larger (for example FIG. 1). Thus, the use of this tool permits an easier quick and positive anastomosis between a bypassed blood vessel and a bypassing blood vessel while a blood flow remaining in a portion between the central and peripheral sides of the bypassed blood vessel is secured during a blood vessel bypass operation.

The statement "the bulky portions are disposed on the conduit eccentrically" means in the present invention, that the bulky portions are formed on the conduit so that the shaft center of the conduit and the substantial center of the circular form formed with the outer edge of the circular bulky portion (hereinafter referred to as shaft center of the bulky portion) are not the same.

By making the shape of the bulky portions circular, when the blood vessel anastomosing auxiliary tool is inserted into a blood vessel, blood leaking from the dissected blood vessel to the side visible during the operation can be prevented and it will not injure the inner wall of the blood vessel. By this point of view, it is preferable that the cross section vertical to the shaft direction of the conduit, formed with the outer edge of the bulky portion, has a circular shape substantively.

Furthermore, it is most preferable that it is a perfect circle or a circular shape close to a perfect circle such as shown in FIGS. 7 and 8, so that it is easy to insert into a blood vessel, and can support equally the inside of a blood vessel. However, the substantially circular cross section is not necessarily limited to a perfect circle, and it has only to be a cross section so that the concept of shaft center could be imagined. For example, the circular arc of the upper half and the lower half of the cross section could be a different shape (for example FIG. 12).

Moreover, the periphery of said circular bulky portion is more preferably to be 1.1-2.0 of the periphery of the hollow conduit.

Next, the second aspect of the present invention will be explained in detail.

The present invention relates to a blood vessel anastomosing auxiliary tool characterized by, in addition to said constituent features of the blood anastomosing auxiliary tool of the present invention, having a flexible guide wire 13 guiding said hollow conduit when inserting into a blood vessel; having a higher elasticity than the blood vessel to which the guide wire 13 would be inserted; the width being adjustable to be inserted into the lumen of the hollow conduit; and the length being more than 1.2 times longer than the length of the hollow conduit (shaft direction).

As for the blood vessel anastomosing auxiliary tool of the present invention, the guide wire 13 being inserted to the hollow conduit 12, the flexibility of the blood vessel anastomosing auxiliary tool 1 becomes higher as a whole. As the diameter of the guide wire 13 is smaller than the diameter of the hollow conduit 12, it would be easier to insert the hollow conduit 12 than inserting it without the guide wire 13, alone into a blood vessel. Especially, in many cases, it is convenient to use the tool wherein the guide wire 13 is inserted into the hollow conduit 12 in advance, and the ends of the guide wire 13 is projected from the ends of the hollow conduit, because the (projected) guide ends are to be inserted into a blood vessel.

However, as there is some cases that the guide wire 13 is not necessary, it is possible to put the guide wire 13 and the hollow conduit 12 in the same bag separately, to sterilize and to insert the guide wire 13 into the hollow conduit 12 according to need. In addition, "a width being adjustable" mentioned above, means that the guide wire 13 can freely be inserted, retrieved, go through the lumen of the hollow conduit 12, and more specifically that the outer diameter of the guide wire 13 is smaller than the inner diameter of hollow conduit 12.

Next, the above described third aspect of the invention will be explained in detail.

The present invention relates to a blood vessel anastomosing auxiliary tool, according to the above described constituent features of the blood vessel anastomosing auxiliary tool of the present invention, wherein one end of said retrieving means is attached to said hollow conduit, and to the other end is attached a tab wherein a holding auxiliary means and a tissue-binding auxiliary means are disposed.

The holding auxiliary means and the tissue-binding auxiliary means could be a means which serves as both holding auxiliary means and tissue-binding auxiliary means. As for means which serves as both a holding auxiliary means and an tissue-binding auxiliary means, a through-hole formed on the tab could be exemplified.

Furthermore, for said through-hole, it is preferable that the diameter is between 1 and 5 mm, and it is formed at 0.5-10 mm from the edge of the tab.

BEST MODE OF CARRYING OUT THE INVENTION

Figure 7:
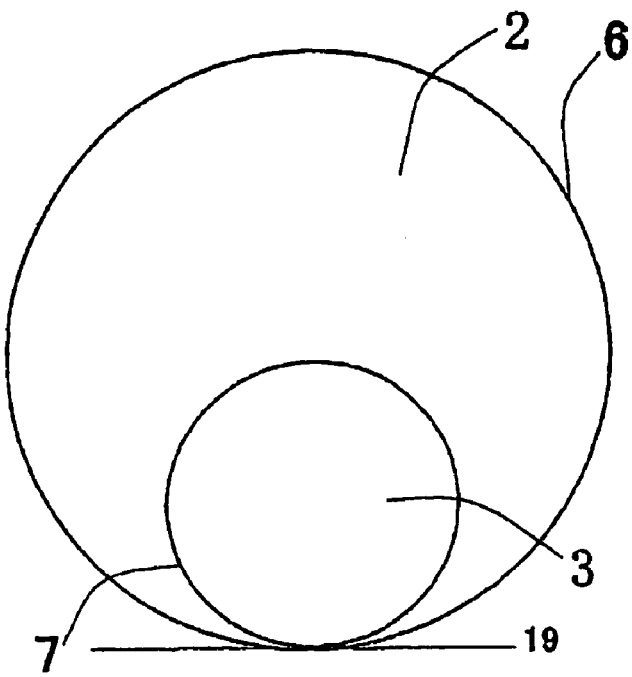
FIG. 7 is a schematic diagram showing a situation wherein a part of the outer edge of the bulky portion of the blood vessel anastomosing auxiliary tool of the present invention is touching the outer edge of the non-bulky portion.
Figure 8:
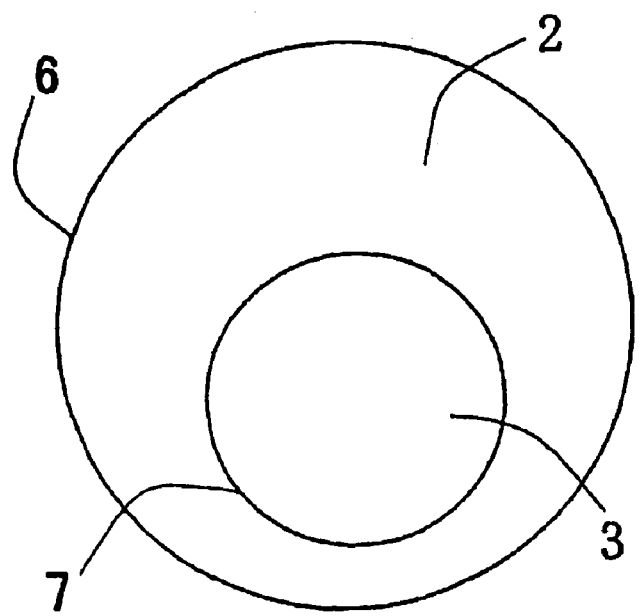
FIG. 8 is a schematic diagram to show the bulky portion of the blood vessel anastomosing auxiliary tool of the present invention, wherein the eccentricity is low.

Concerning the blood vessel anastomosing auxiliary tool 1 of the present invention, in order to obtain a larger space for the suture needle to pass when anastomosing blood vessel, the bulky portion 2 is disposed eccentrically on the hollow conduit 12 as described above (FIGS. 1-9), and when the eccentricity is larger, a higher effect can be obtained. That is, compared with the small eccentricity as shown in FIG. 8, it is preferable that the eccentricity is larger, such as the one shown in FIG. 7. Especially, as shown in FIG. 7, when the eccentricity is large and that a part of the outer edge 6 of the bulky portion 2 is touching the extrapolation line 19 of the outer edge 7 of the non-bulky portion 3, when anastomosing blood vessel, not only a larger space for the suture needle to pass may be formed but it is preferable because it could be also effective for the hemostasis during the blood vessel anastomosing.

Further more, generally 2 bulky portions are disposed for bulky portion 2, but in some cases, it is possible to dispose more than 2, for example 3 bulky portions. In such case, at least 1 bulky portion 2 can be disposed eccentrically, but when 2 bulky portions 2 exist, it is preferable to dispose eccentrically both the 2 bulky portions 2. In case that both 2 bulky portions 2 are disposed eccentrically, by forming and disposing eccentrically each bulky portions substantially on the same side of the conduit 2, the space 5 formed between the inner wall of the blood vessel 11 and the blood vessel anastomosing auxiliary tool 1 is larger, compared to when the bulky portions are not disposed on the same side. For the statement "disposing eccentrically each bulky portions 2 substantially on the same side of the conduit 12", it is defined as follows.

Figure 9:
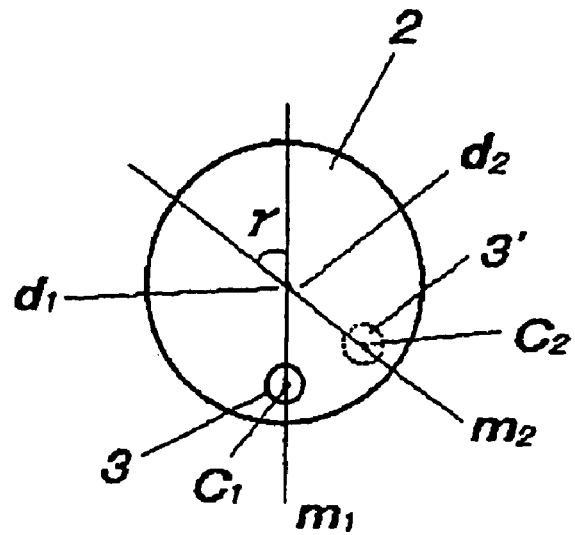
FIG. 9 is a schematic diagram showing the twist level of eccentricity direction lines of each bulky portion of the blood vessel anastomosing auxiliary tool of the present invention.
Figure 10:
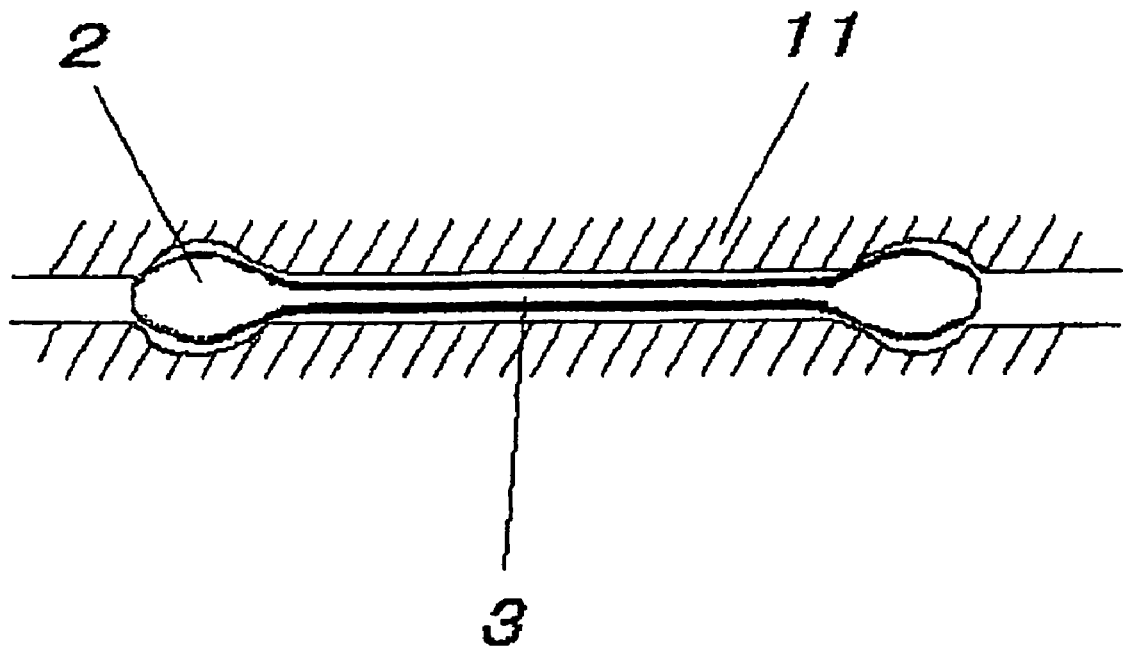
FIG. 10 is a schematic diagram to show the shape of the bulky portion of the conventional blood vessel anastomosing auxiliary tool.
Figure 11:
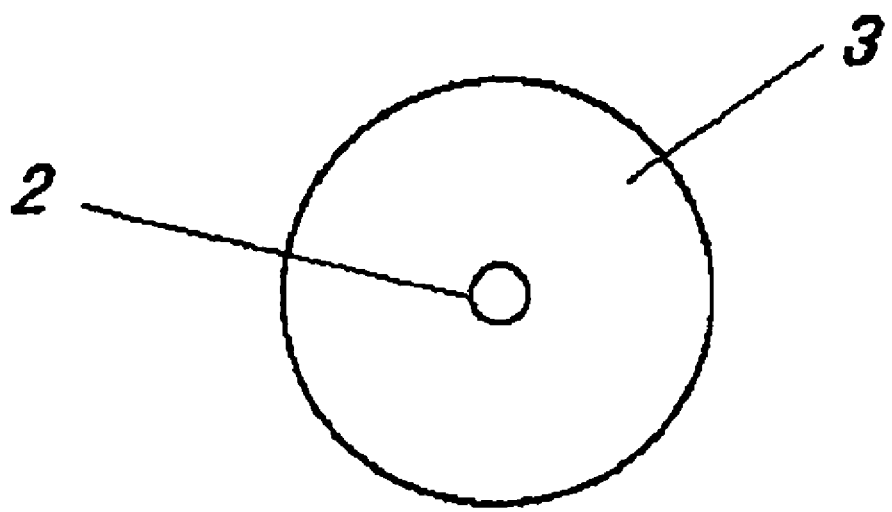
FIG. 11 is a schematic diagram of the cross section, vertical to the shaft of the bulky portion of the conventional blood vessel anastomosing auxiliary tool.
Figure 12:
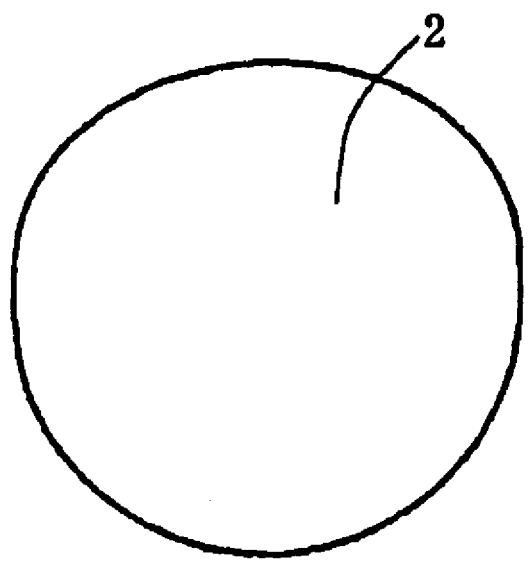
FIG. 12 shows a cross section of the bulky portion of the blood vessel anastomosing auxiliary tool of the present invention, wherein the shape of the arc of the upper half and the lower half is different.

As shown in FIG. 9, the straight line connecting $C_1$, which corresponds to the shaft center of the conduit 3 and $d_1$ which is the shaft center of the bulky portion 2 is the eccentric direction line, and when m1 is the eccentric direction line of 1 bulky portion 2, $m_2$ is the eccentric direction line of the other bulky portion 2, as it is shown in FIG. 9, it refers to a situation that the twist angle γ made by $m_1$ and $m_2$ is within ±45 degrees, but it is preferable that said angle is smaller, most preferably 0 degree.

Figure 6:
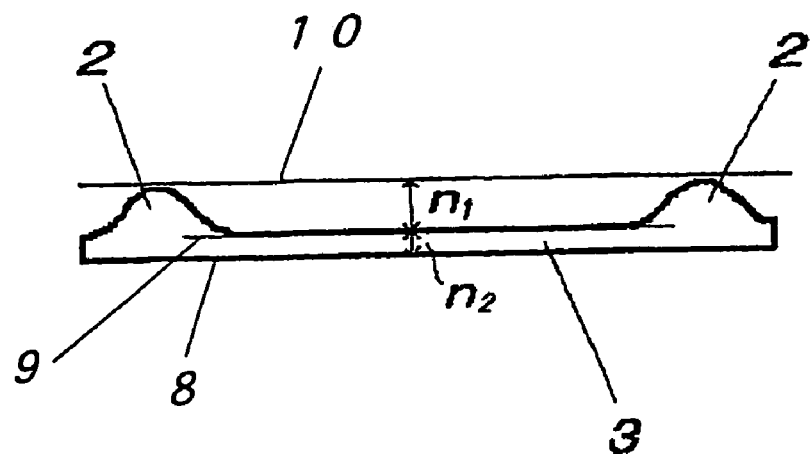
FIG. 6 is a schematic diagram to show the relation between the outer diameter of the non-bulky portion: $n_2$ and the height of the bulky portion: $n_1$ of the blood vessel anastomosing auxiliary tool of the present invention.

Furthermore, as for the height n1 of the bulky portion, as it is shown in FIG. 6, when $n_2$ is the distance from the bottom surface 8 to the upper outer surface 9 of the non-bulky portion of the conduit (that is the outer diameter of the non-bulky portion), and $n_1$ is the distance from the upper outer surface 9 to the uppermost surface 10 of the bulky portion of the non-bulky portion (the height of the bulky portion), it is preferable that $n_1/n_2$ is between 0.20 and 3.0. When said $n_1/n_2$ is less than 0.20, the space 5 formed between the inner wall of the blood vessel 11 and the blood vessel anastomosing auxiliary tool 1 (the non-bulky portion 3 of the conduit between the 2 bulky portions) could not be large, and when $n_1/n_2$ exceeds 3.0, the flow volume running in the conduit would be too small.

As for the shape of the bulky portion 2, as it is necessary to retrieve the blood vessel anastomosing auxiliary tool from within a blood vessel just before the blood vessel anastomosing is finished, it is preferable to be in a shape so that it doesn't injure the inner wall of the blood vessel 11 or not to hook the suture when retrieving the tool.

Figure 1:
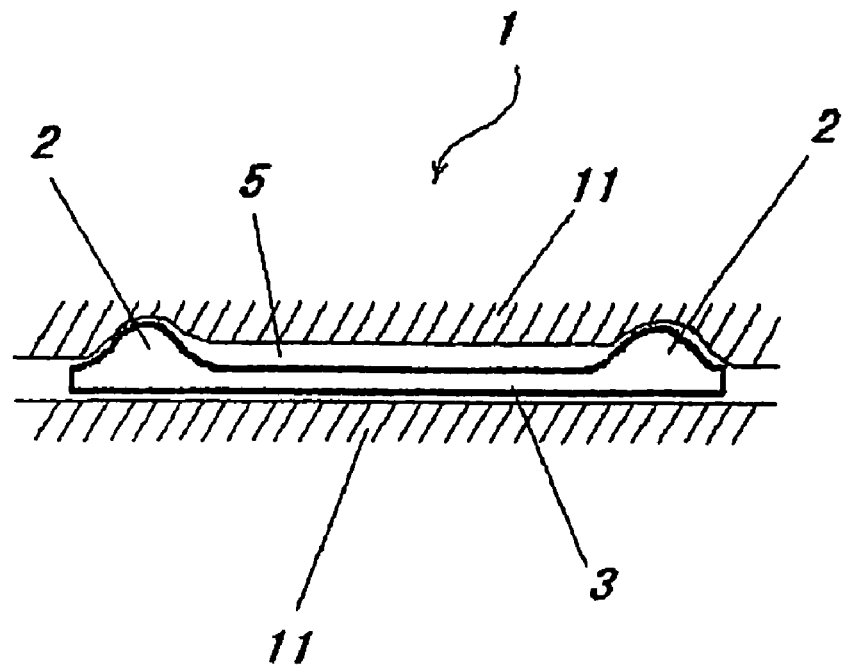
FIGS. 1, 2 and 3 are schematic diagrams showing the shape of the bulky portion of the blood vessel anastomosing auxiliary tool of the present invention.
Figure 2:
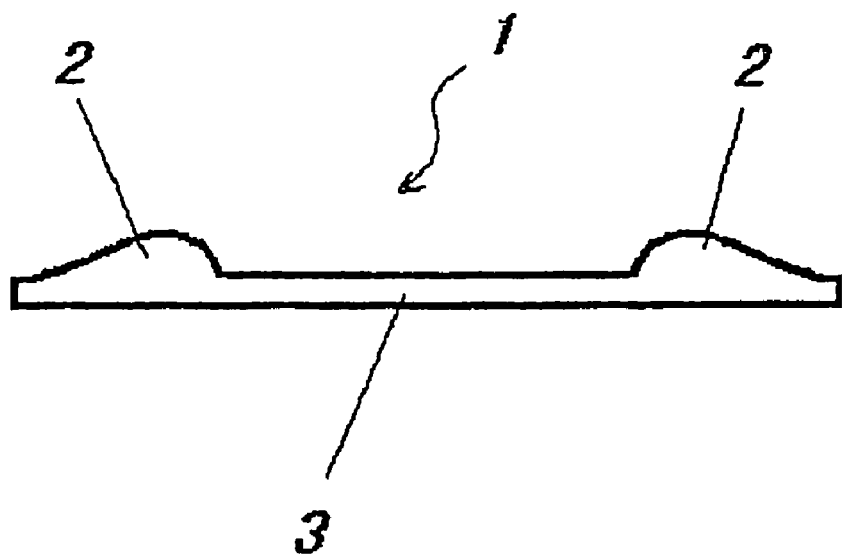
Figure 3:
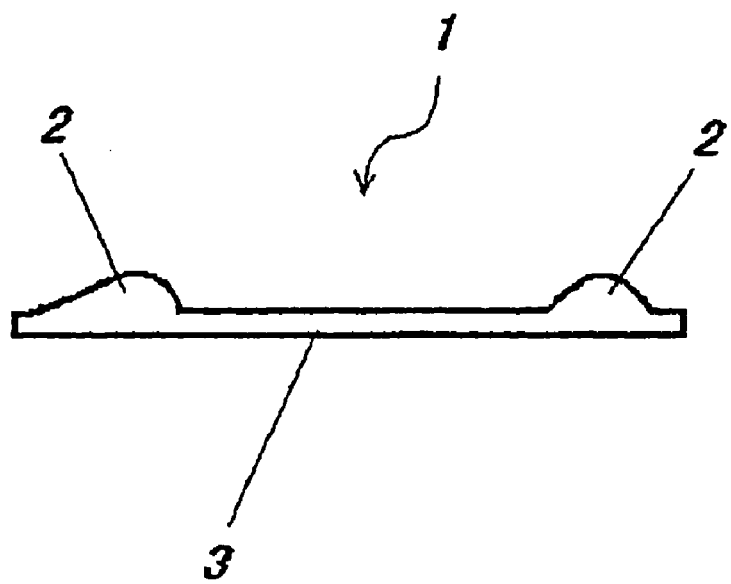
Figure 4:
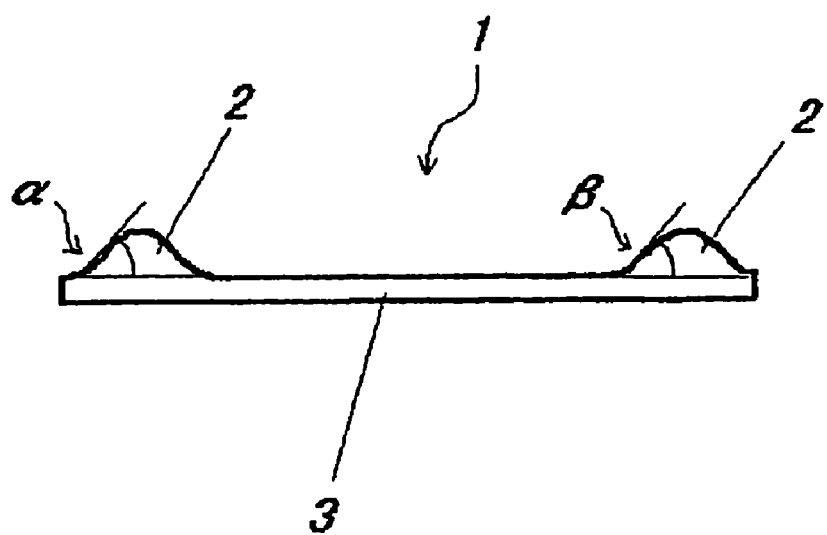
FIG. 4 is a schematic diagram to show the inserting angle α and the retrieving angle β of said bulky portion.
Figure 5:
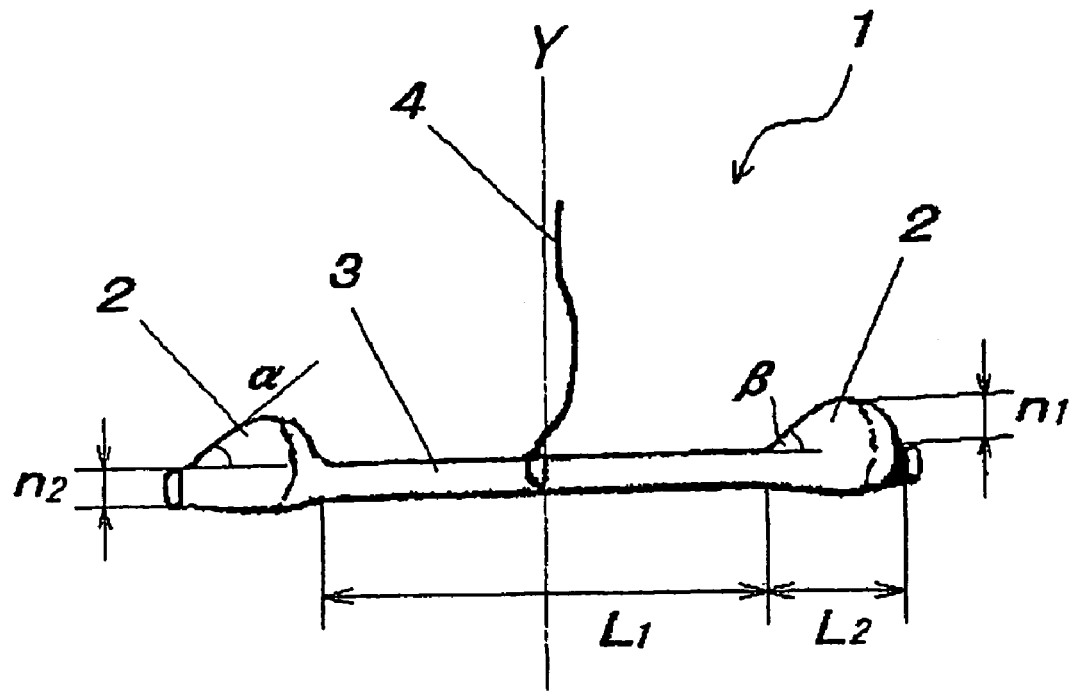
FIG. 5 is a schematic diagram to show the shape and the size of the blood vessel anastomosing auxiliary tool of the present invention.

As for a shape preferable for the bulky portion 2, a shape of drop (tear drop) can be exemplified. Examples of a shape of drop (tear drop) include: as shown in FIGS. 1, 4 and 6, when the 2 bulky portions 2 have identical shape, each of the bulky portion 2 being bilaterally symmetric against the shaft direction of the conduit; as shown in FIG. 2, when the 2 bulky portions 2 have identical shape, each of the bulky portions not being bilaterally asymmetric against the shaft direction of the conduit; and as shown in FIGS. 3 and 5, when the shape of the 2 bulky portions 2 are not identical. However, the shape of the bulky portion 2 of the present invention will not be limited to these figures.

Moreover, it is preferable that the interface (portion) of bulky portion 2 and non-bulky portion 3 are connected with a curved line to be smoothly joined with the hollow conduit, to prevent touching the blood vessel wall when inserting or retrieving the tool. In said bulky portion 2, the inserting angle is α as it is shown in FIGS. 4 and 5, and the retrieving angle is β. The inserting angle α mentioned here, refers to the angle made between the arc touching the blood vessel wall of the bulky portion 2 and the shaft of the non-bulky portion (conduit) 3, wherein said bulky portion 2 is at the side where the blood vessel anastomosing auxiliary tool 1 of the present invention is inserted into a blood vessel (for example the coronary artery). The retrieving angle is the angle made between the arc of the bulky portion 2, touching with the non-bulky portion (conduit) 3, wherein said arc of the bulky portion 2 touches the blood vessel wall just before the retrieving of the blood vessel anastomosing auxiliary tool 1 of the present invention from within a blood vessel (for example the coronary artery).

Moreover, as for the inserting angle α, when the inserting angle α of the bulky portion shown in FIG. 4 exceeds 45 degrees, the hollow conduit 12 would easily touch the blood vessel wall when retrieving the blood vessel anastomosing auxiliary tool 1 from within the blood vessel, therefore, it is preferable to be between 1 and 60 degrees. On the other hand, when the angle is smaller than 20 degrees, the total length of the hollow conduit 12 would be long, therefore it is more preferable for the inserting angle to be between 20 and 45 degrees. Moreover, when the retrieving angle β of the bulky portion shown in FIG. 4 exceeds 46 degrees, the hollow conduit 12 would easily touch the blood vessel wall when inserting or retrieving the blood vessel anastomosing auxiliary tool into or from within the blood vessel, and when the retrieving angle β is smaller than 19 degrees, the space 5 would be small, therefore it is preferable to be between 20 and 45 degrees.

As for the material of the bulky portion 2, any synthetic resin material can be used, but materials that would hardly injure the inner wall of the blood vessel, such as ethylene-vinyl acetate copolymer (EVA), polyamide, silicone and the like are preferable. The bulky portion can be formed with different material from the non-bulky portion of the conduit, but it is preferable that it is made from the same material with non-bulky portion 3, and moreover it is preferable that both bulky portion 2 and non-bulky portion 3 have a shore hardness determined by JIS (Japanese Industry Standard) around 20-80 D. When said hardness is below 50, the tube may easier kink in the blood vessel, and when it is higher than 70 D, it may injure the inner wall of the blood vessel.

Figure 13:
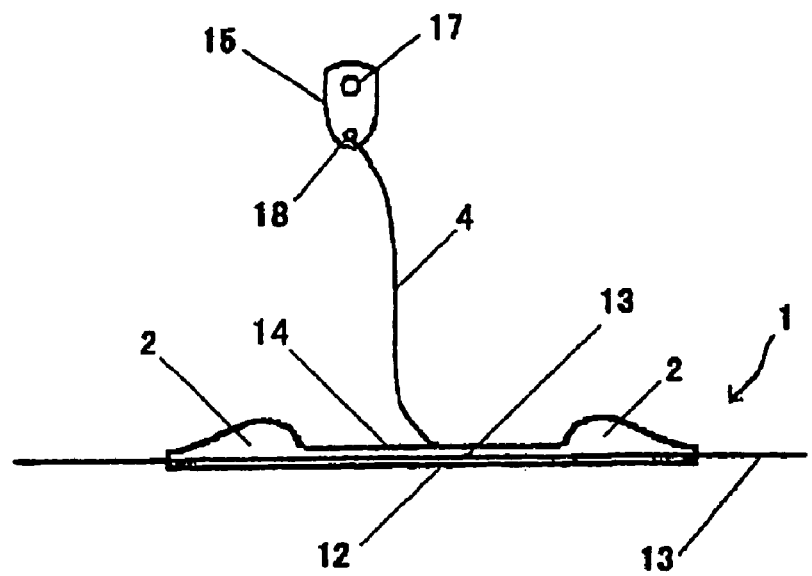
FIG. 13 is a schematic diagram showing an example of a blood vessel anastomosing auxiliary tool having a guide wire 13 of the present invention.
Figure 14:
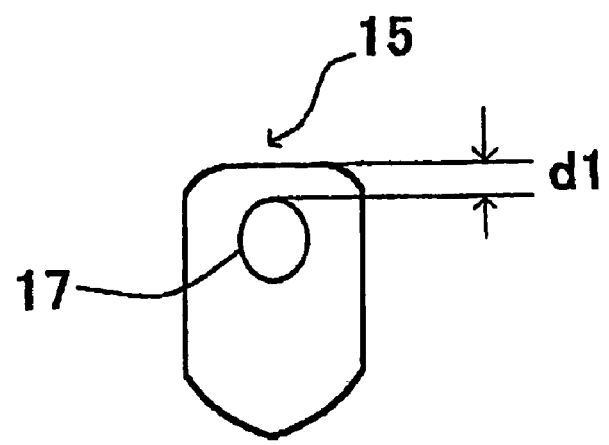
FIG. 14 is a schematic diagram of the tab of a blood vessel anastomosing auxiliary tool of the present invention.

In FIG. 13, the blood vessel anastomosing auxiliary tool 1 using the guide wire 13 is shown, and in FIG. 14, the tab 15 to be used for the blood vessel anastomosing auxiliary tool 1 of FIG. 13 is shown. The blood vessel anastomosing auxiliary tool 1 of FIG. 13 is mostly composed of the hollow conduit 12 and the guide wire 13.

For the blood vessel anastomosing auxiliary tool 1 of FIG. 13, it is preferable that the guide wire 13 has a higher degree of elasticity than the hollow conduit 12. However, the guide wire 13 requires a predetermined elasticity when inserting into the blood vessel, but if it is too hard, it could injure the inner wall of the blood vessel, therefore, the shore hardness of said guide wire 13 is preferably to be between 30-80 D, more preferably 40-50 D. Moreover, as for the length of the guide wire 13, it would not possible to achieve said aim if it is too short, but be disturbing and a loss if it is too long, therefore it is preferable to be 1.2-5 times longer than the length of the shaft direction of the hollow conduit 12.

A towing string 4 to which tab 15 is attached to one end, is attached to the central part 14 of the hollow conduit 12, a penetrating through-hole 17 and an eyelet 18 are formed on the tab 15. Both sides of the guide wire 13 are inserted into the lumen of hollow conduit 12, projecting both ends from both ends of the hollow conduit 12. Both ends of the hollow conduit 12 are swollen in a circular form, and these 2 bulky portions 2 are formed with a smooth curve on both ends. One end of the towing string 4 is attached to the central part 14 of the hollow conduit 12, and the other end is attached to the eyelet 18 formed on tab 15.

Said guide wire 13 is made from polyamide resin, and has flexibility and self-restoring property just like the hollow conduit 12.

Said through-hole is preferable to be formed at a distance of 0.5-10 mm from the edge of tab 15 (d1 of FIG. 14), because it makes easy to practice the holding operation of tab 15, for example, it is possible to hold without opening largely the forceps, which is a holding tool.

Next, the example for the use of tab 15 of the blood vessel anastomosing auxiliary tool is described. When retrieving the blood vessel anastomosing auxiliary tool 1 from within the blood vessel, it is necessary to hold the through-hole 17 with forceps and the like and to pull the tab 15. By this way, it is possible to pull the towing string 4 by holding it surely and to retrieve the hollow conduit from within the blood vessel. Furthermore, when practicing the A-C bypass operation, by temporarily attaching the blood vessel anastomosing auxiliary tool in advance by suturing it with a surgical suture to a tissue near the site to be operated, it is possible to use it immediately and have no concern about losing it. It would be easy to attach it temporarily by passing the surgical suture through the through-hole formed on tab 15, and to attach to the tissue with 1 or 2 stitches.

Concerning the retrieving means, as it is shown in FIGS. 5 and 13, it is preferable that it is a fine and strong string 4 attached at the central part of the non-bulky portion. Examples include a string with the shape and size of a fishing line and the like, and the material being silk, polyamide, polyolefin and the like. Moreover, it can be a linear thread in a tubular form as described in Japanese Laid-Open Patent Application No. 2000-5185.

The present invention will be described in detail by the following examples.

EXAMPLE 1

The composition of the blood vessel anastomosing auxiliary tool 1 of FIG. 5 consists of: the non-bulky portion 3 of the hollow conduit 12, made from polyurethane, wherein 2 bulky portions are formed near of each end; and a surgical suture 4 made from silk 5-0 attached to the central part of said non-bulky portion 3. The inner diameter of the non-bulky portion 3 is 0.7 mm, the outer diameter ($n_2$) is 1.0 mm, the length of the central part of the non-bulky portion $L_1$ is 10.0 mm, the length of the shaft direction of the bulky portion $L_2$ is 3.0 mm, and the height of the bulky portion n1 is 1.0 mm. The thickness of the non-bulky portion is 0.15 mm. The inserting angle α of the bulky portion is 45 degrees, the retrieving angle β is also 45 degrees, and the two angles are the same in this example. Moreover, as it can be seen from the figure, both the 2 circular bulky portions 2 are formed at the outer side of the circular conduit 3, and both the 2 bulky portions are formed to be substantially of same shape and size, and are bilaterally symmetric against the center line Y.

EXAMPLE 2

The composition of the blood vessel anastomosing auxiliary tool 1 of FIG. 13 is as follows: the length of the shaft direction of the central part 14 of the hollow conduit 12 (the length excluding the bulky portion) is 12.0 mm, the length of the shaft direction of one bulky portion 2 is 2.5 mm. The whole hollow conduit is made from polyamide resin, and has flexibility and self-restoring property (that is, even if bend by force, by releasing it, it would go back straight as it was by it self). The outer diameter of the bulky portion 2 is around 1.5 mm (the inner diameter is around 0.5 mm), the outer diameter of the central part 14 is around 0.7 mm (the inner diameter is the same as the bulky portion). The outer diameter of the guide wire 13 is around 0.4 mm, the length is 50.0 mm and it is made from polyamide resin just like the hollow conduit.

INDUSTRIAL APPLICABILITY

According to the present invention, a blood vessel anastomosing auxiliary tool having beneficial effects including the following points can be obtained:

1. By disposing the bulky portion eccentrically on the conduit, a large space is formed between the inner wall of the blood vessel and the anastomosing auxiliary tool when anastomosing blood vessel, thus, the surgical suture can pass easier compared to conventional tools. Therefore, the operation becomes easy and ensuring, and the time needed for is reduced.

2. As for the auxiliary tool of the present invention, the bulky portion and the non-bulky portion of the conduit are joined with a smooth curved line in a shape of tear drop, therefore there is no concern about injuring the lining of the blood vessel when inserting or retrieving the tool, and these operations can be practiced easily.

3. By using the guide wire with the hollow conduit, the hollow conduit may be inserted more easily into the lumen of the blood vessel. Furthermore, by disposing holding means or tissue-binding means to the tab attached to the hollow conduit, it is possible to pull the hollow conduit by holding it tightly, and also to prevent losing the anastomosing auxiliary tool beforehand.

The invention claimed is:

1. A blood vessel anastomosing auxiliary tool, comprising:
a hollow conduit having openings only at both ends, and having flexibility and self-restoring property for inserting into a blood vessel;
a blood leaking preventer to prevent blood leaking from a space formed between the external wall of said conduit and an inner wall of the blood vessel, when the hollow conduit is inserted into the blood vessel; and
a retrieving means for retrieving said conduit from within the blood vessel,
wherein said blood leaking preventer satisfies following (a) to (e):
(a) said blood leaking preventer comprises first and second bulky portions which are formed at both ends of said hollow conduit, each of said first and second bulky portions having a diameter larger than that of non-bulky portion of the hollow conduit;
(b) the bulky portions are disposed eccentrically with respect to a central axis of the hollow conduit;
(c) a twist angle $\gamma$ is within ±45 degrees, where the twist angle $\gamma$ is a crossing angle made by a line $m_1$ and a line $m_2$, where the line $m_1$ is an eccentric line which formed by connecting a central axis of the hollow conduit and a central axis of the first bulky portion, and the $m_2$ is an eccentric line which formed by connecting a central axis of the hollow conduit and a central axis of the second bulky portion;
(d) an inserting angle $\alpha$ of the bulky portions is between 20 and 45 degrees; and
(e) a retrieving angle $\alpha$ of the two circular bulky portions is between 19 and 45 degrees.

2. The blood vessel anastomosing auxiliary tool according to claim 1, wherein the retrieving means for retrieving said conduit from within a blood vessel is a linear thread attached near the central part of the hollow conduit.

3. The blood vessel anastomosing auxiliary tool according to claim 1, wherein the first and second bulky portions of the blood leaking preventer have a cross section of substantially elliptical shape along the axis of the hollow conduit.

4. The blood vessel anastomosing auxiliary tool according to claim 1, wherein one part of the outer edge of the first and second bulky portions is touching the outer edge of the non-bulky portion.

5. The blood vessel anastomosing auxiliary tool according to claim 1, wherein n1/n2 is between 0.20 and 3.0, when n2 is a diameter of the non-bulky portion, and n1 is the height of the first and second bulky portions.

* * * * *